(12) United States Patent
Huang et al.

(10) Patent No.: US 10,441,153 B2
(45) Date of Patent: *Oct. 15, 2019

(54) ENDOCRANIAL ENDOSCOPE

(71) Applicant: CLEARMIND BIOMEDICAL, INC., San Jose, CA (US)

(72) Inventors: Po-Hao Huang, San Jose, CA (US); Feng-Cheng Chang, San Jose, CA (US); Sheng-Chi Lin, Taipei (TW)

(73) Assignee: Clearmind BioMedical, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/959,594

(22) Filed: Apr. 23, 2018

(65) Prior Publication Data

US 2018/0235441 A1    Aug. 23, 2018

Related U.S. Application Data

(63) Continuation-in-part of application No. 15/364,952, filed on Nov. 30, 2016, now Pat. No. 9,968,249.

(Continued)

(51) Int. Cl.
*A61B 1/00* (2006.01)
*A61B 1/05* (2006.01)
(Continued)

(52) U.S. Cl.
CPC ............ *A61B 1/313* (2013.01); *A61B 1/0051* (2013.01); *A61B 1/0052* (2013.01);
(Continued)

(58) Field of Classification Search
None
See application file for complete search history.

(56) References Cited

U.S. PATENT DOCUMENTS 4,624,243 A    11/1986 Lowery
5,431,635 A *  7/1995 Yoon .................. A61B 10/0233
                                                  604/164.12
(Continued)

FOREIGN PATENT DOCUMENTS

WO    WO2010126586    11/2010
WO    WO2013082497    6/2013

OTHER PUBLICATIONS

Michael R. Gaab, Instrumentation: Endoscopes and Equipment, World Neurosurgery 79 [2S]: S14.e11-S14.e21, Feb. 2013 www.Worldneurosurgery.org.

(Continued)

*Primary Examiner* — Aaron B Fairchild
(74) *Attorney, Agent, or Firm* — Cooper & Dunham LLP

(57) ABSTRACT

An endoscope particularly suited for endocranial procedures and a method of using the endoscope. In some examples the endoscope is rigid except for a bend/tilt portion near a distal end of a rigid tube that is inserted in a patient's cranium, which distal end is controlled in a degree and direction of tilt with a finger operated controller at the endoscope's handle. Some examples use telescoping tubes that allow customizing the endoscope size for specific procedures. A distal portion of the endoscope can be disposable, supplied in a sterile package for a single procedure, thus taking into account contamination dangers that are particularly high for intracranial and certain other interventions and the fact that it can be difficult or impossible to effectively autoclave heat-sensitive components of certain endoscopes or effectively sterilize them using other techniques.

15 Claims, 17 Drawing Sheets

Related U.S. Application Data which is a continuation-in-part of application No. PCT/US2015/052152, filed on Sep. 25, 2015.

(60) Provisional application No. 62/299,307, filed on Feb. 24, 2016, provisional application No. 62/084,584, filed on Nov. 26, 2014, provisional application No. 62/063,114, filed on Oct. 13, 2014, provisional application No. 62/056,617, filed on Sep. 29, 2014.

(51) Int. Cl.
    *A61M 1/00*     (2006.01)
    *A61B 1/005*     (2006.01)
    *A61B 1/015*     (2006.01)
    *A61B 1/313*     (2006.01)
    *A61B 1/317*     (2006.01)
    *A61B 17/00*     (2006.01)

(52) U.S. Cl.
CPC ........ *A61B 1/0055* (2013.01); *A61B 1/00066* (2013.01); *A61B 1/00068* (2013.01); *A61B 1/00085* (2013.01); *A61B 1/00103* (2013.01); *A61B 1/00135* (2013.01); *A61B 1/00142* (2013.01); *A61B 1/015* (2013.01); *A61B 1/317* (2013.01); *A61M 1/0064* (2013.01); *A61B 1/00045* (2013.01); *A61B 1/00094* (2013.01); *A61B 1/00165* (2013.01); *A61B 1/05* (2013.01); *A61B 2017/00991* (2013.01)

(56) References Cited

U.S. PATENT DOCUMENTS

| | | | |
|---|---|---|---|
| 2004/0082969 A1* | 4/2004 | Kerr | A61B 17/0218 606/205 |
| 2004/0167542 A1 | 8/2004 | Solar | |
| 2008/0154181 A1 | 6/2008 | Khanna | |
| 2008/0281293 A1* | 11/2008 | Peh | A61B 1/00082 604/523 |
| 2009/0054733 A1 | 2/2009 | Marescaux | |
| 2009/0198216 A1 | 8/2009 | Muni | |
| 2010/0022824 A1 | 1/2010 | Cybulski | |
| 2012/0330196 A1 | 12/2012 | Nita | |
| 2014/0148729 A1 | 5/2014 | Schmitz | |

OTHER PUBLICATIONS

Henry W.S. Schroeder, M.D., Ph.D., A New Multipurpose Ventriculoscope Neurosurgery vol. 62 Feb. 2008.

* cited by examiner

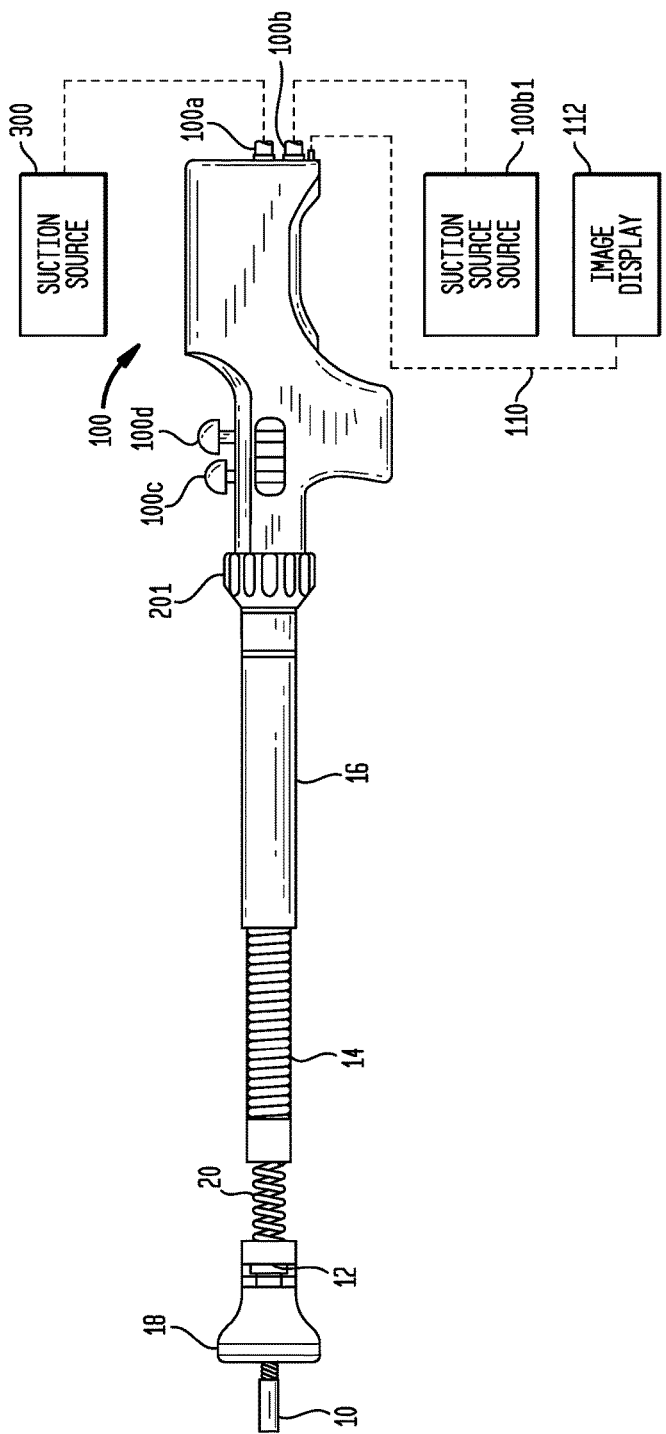
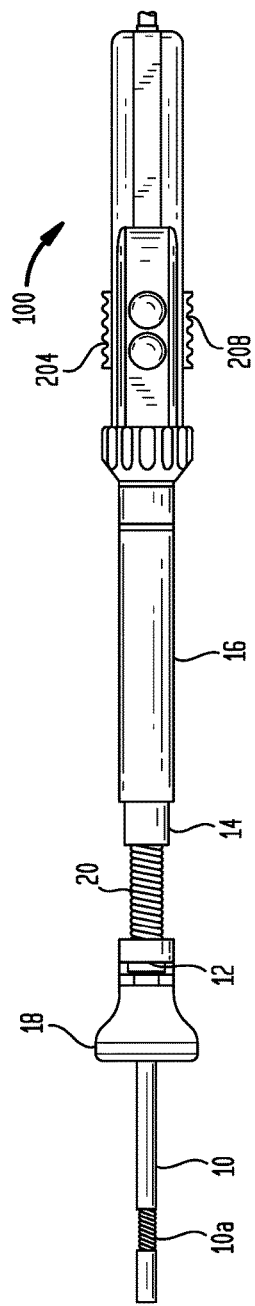
FIG. 1a
FIG. 1b

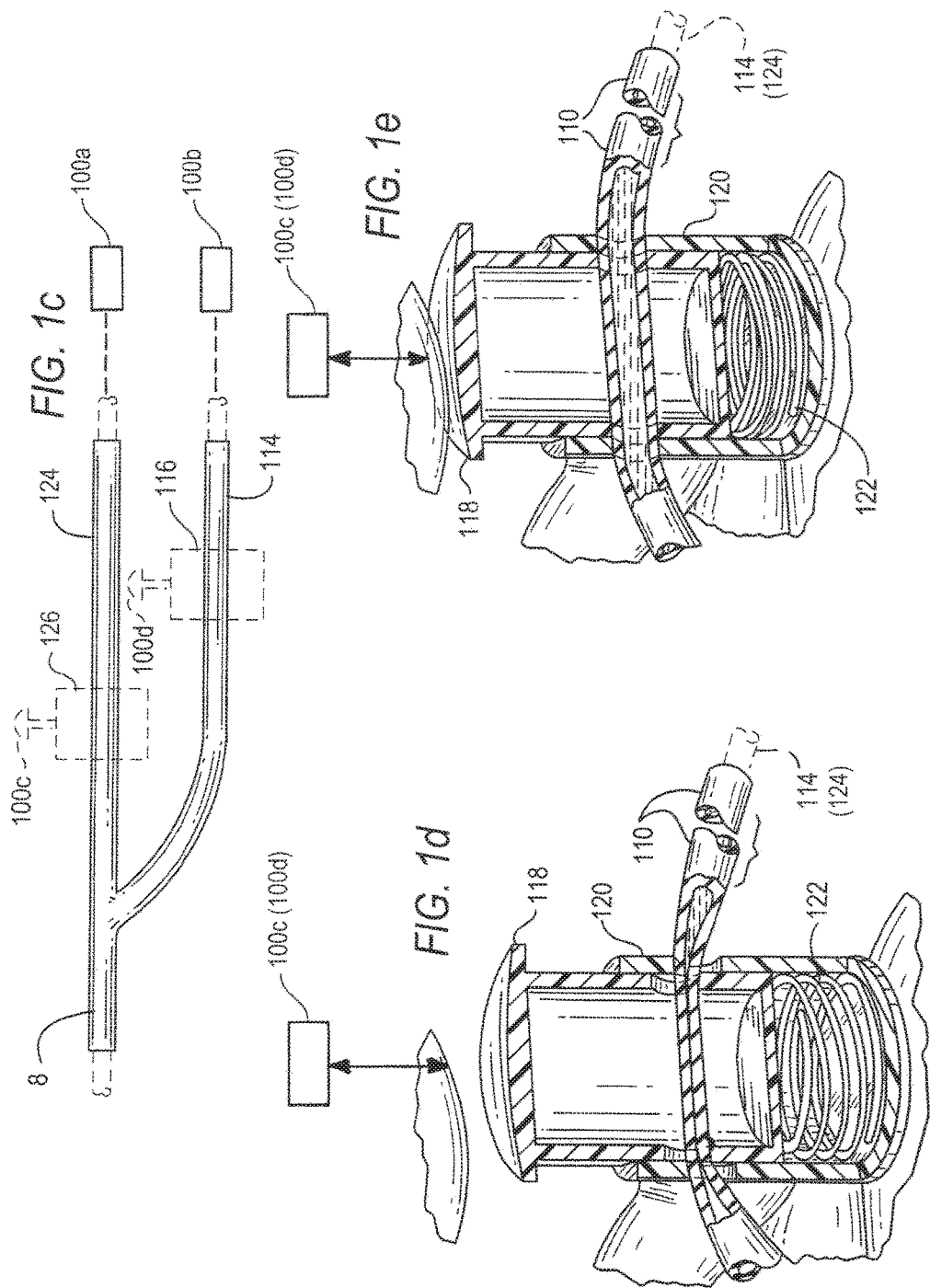

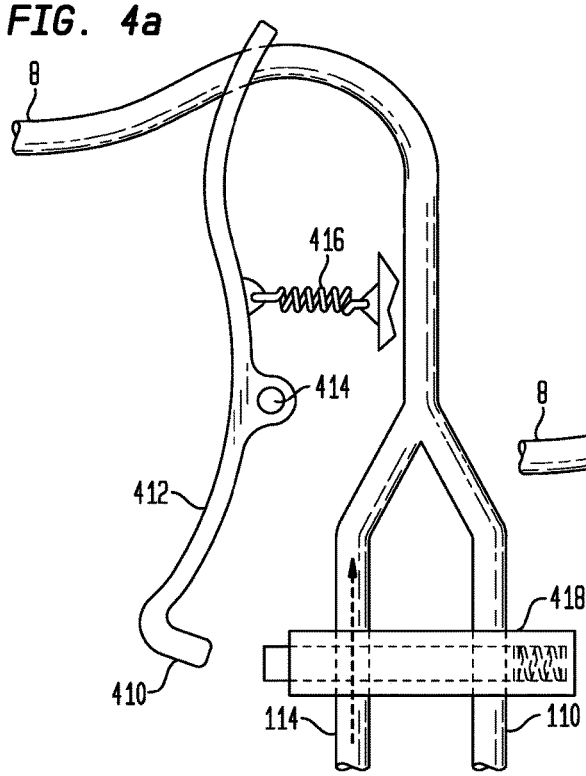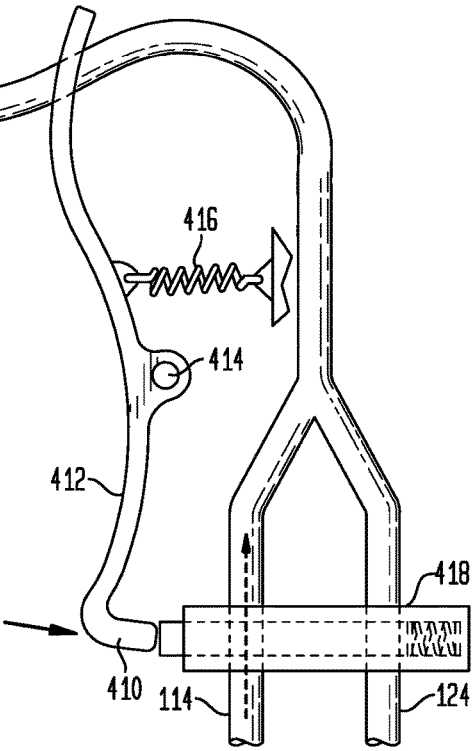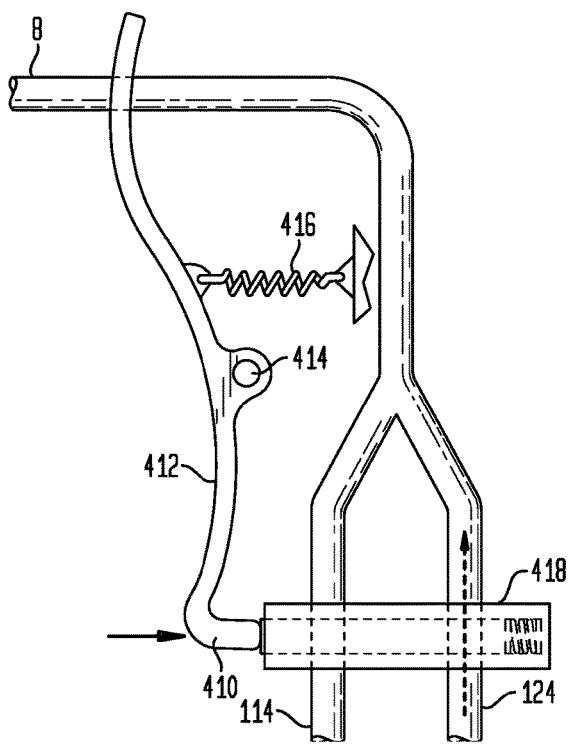

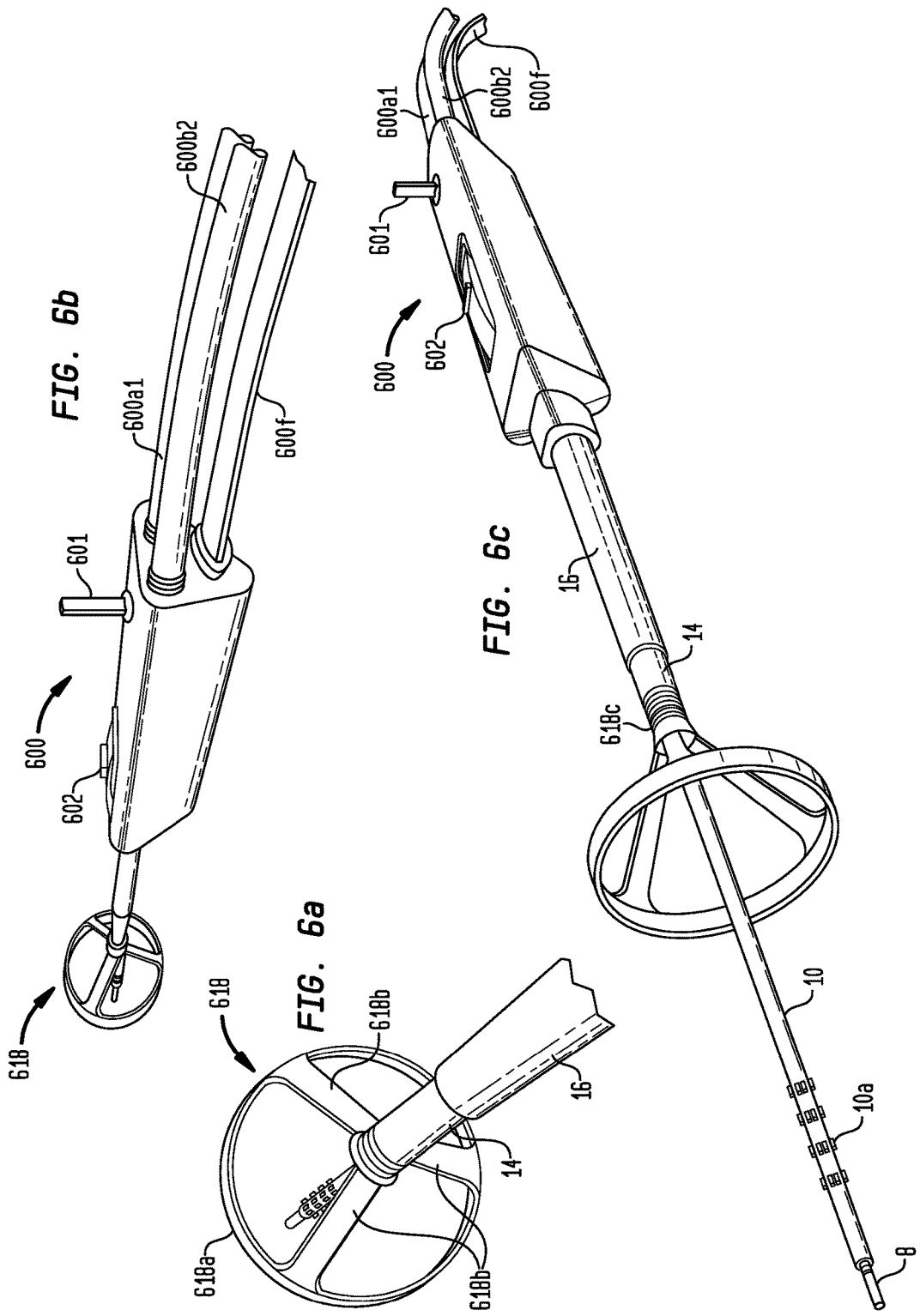

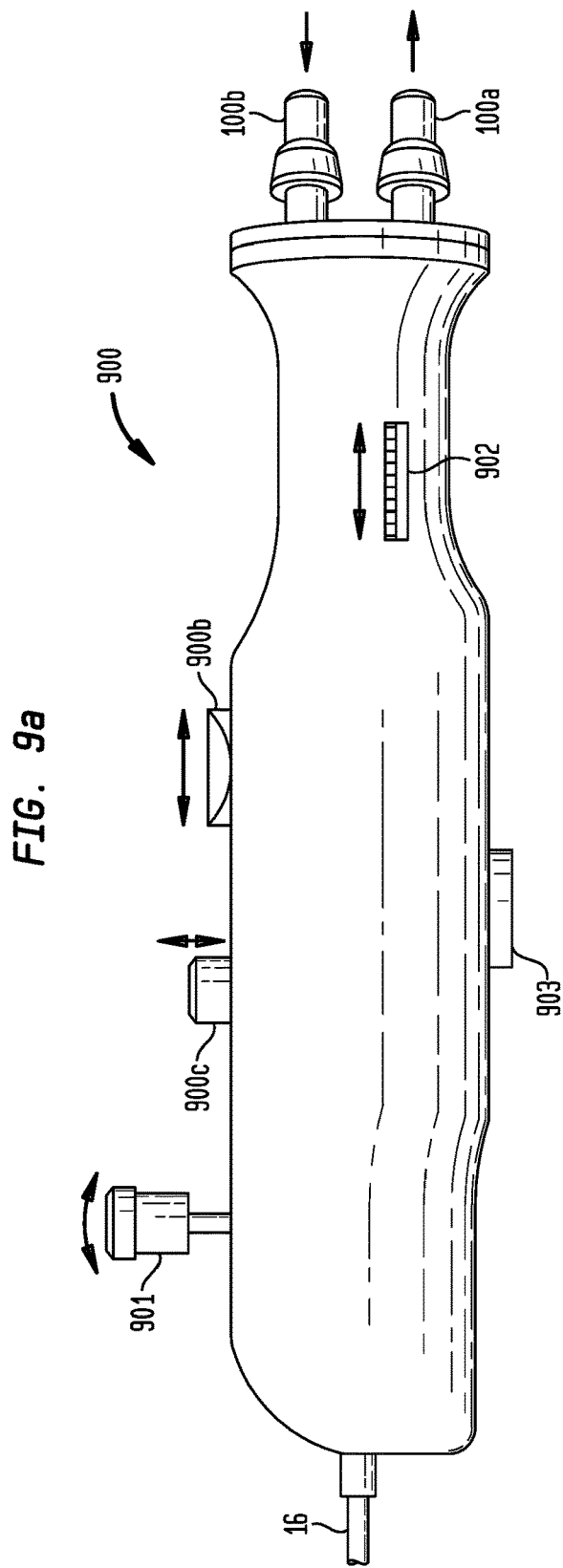

ENDOCRANIAL ENDOSCOPE

REFERENCE TO RELATED APPLICATIONS

This patent application is a continuation-in-part of U.S. application Ser. No. 15/364,952 filed Nov. 30, 2016 and allowed Jan. 26, 2018, which (a) claims the benefit of U.S. Provisional Applications No. 62/299,307 filed Feb. 24, 2016, and (b) is a continuation-in-part of PCT application PCT/US2015/52152 filed Sep. 25, 2015 that claims the benefit of U.S. Provisional Applications Nos. 62/056,617 filed Sep. 29, 2016, 62/063,114 filed Oct. 13, 2014, and 62/084,584 filed Nov. 26, 2014. This patent specification incorporates by reference the patent applications identified in this paragraph, as well as the other publications, including patents and published patent applications and unpublished patent applications, identified throughout the rest of this patent specification.

FIELD

This patent specification is in the field of endocranial endoscopy and certain aspects of the disclosed equipment and methods additionally pertain to otorhinolaryngological surgery, skull base surgery, and neurosurgery in general.

BACKGROUND

Endocranial endoscopes are surveyed in Gaab M R, *Instrumentation: Endoscopes and Equipment*, World Neurosurgery 79[2s]: S14.E1-S14.E21, February 2013. Another example of intracranial endoscopes is discussed in Schroeder H W S, *A New Multipurpose Ventriculoscope*, Neurosurgery, Vol. 62, Number 2, February 2008, 489-492. Other examples of endoscopes are discussed in US 1010/0022824 A1, WO 2013/082497 A1, US 2012/0330196 A1, US 2009/0054733 A1, 2009/0198216 A1, WO 2010/126586 A1, US 2004/0167542, US 2008/0154181 A1, and US 2014/0148727 A1.

SUMMARY OF DISCLOSURE

Disclosed are endoscopes particularly suited for endocranial procedures. Some of the disclosed examples are rigid except for a bend/tilt portion near a distal end of a portion that is inserted into a patient's cranium and is controlled to perform bi-directional tilt within a specified degree, using a controller at the endoscope's handle. Some examples use telescoping tubes that allow customizing the endoscope size for specific procedures. Some examples of the described endoscopes are disposable, single-use devices or at least have major portions that are disposable, to avoid contamination dangers that are particularly high for intracranial and certain other interventions. The portions of traditional endoscopes that go into the cranium can be difficult to sterilize effectively and efficiently in an autoclave, especially when they include heat-sensitive components.

One disclosed example is an endocranial endoscope comprising: an internally threaded, rigid outer tube (16) having proximal and distal portions; an externally threaded middle rigid tube (14) threaded into the outer tube for relative rotation therewith to thereby telescope between extended and retracted positions; an inner tube (10) that has a proximal portion partly in middle tube (14) and a distal portion that is shaped, dimensioned, and configured for insertion into a patient's cranium; a stopper (18, 618k) mounted distally of the middle tube to move axially relative to the middle tube, and a biasing element (20) biasing the stopper toward the distal direction; wherein the inner tube has a bend/tilt portion (10a) adjacent a distal end thereof, and extended and retracted positions relative to the middle tube; a suction/irrigation tube (8, 8a) sliding in the inner tube between an extended position in which it protrudes distally from the inner tube and a retracted position; an illumination module (701, 702; 802, 803) and an imaging module (703, 801) at a distal end of the inner tube, wherein the illumination module is configured to illuminate a field of view inside the patient's cranium and the imaging module is configured to take and supply images of the field of view for display to a user; a handle (100, 500, 600, 900) configured to be grasped by a user's hand and having a distal portion coupled to a proximal portion of the outer tube, and a proximal portion, said handle comprising a suction port coupler (100a) and an irrigation port coupler (100b) at a proximal portion of the handle, and the following user-operated controllers: (i) one or more suction and irrigation controllers (100c, 100d, 410, 418a, 418b, 418c, 502, 602, 900c, 900d) configured to control flow between the suction/irrigation tube and the suction and irrigation ports, (ii) a tilt/bend controller (201, 301, 501, 601, 901) operatively associated with the tilt/bend portion of the inner tube to control direction and degree of tilt/bend thereof; and (iii) an extension-retraction controller (204, 208, 410, 412, 414, 416) operatively associated with the suction/irrigation tube to control a degree by which a distal end of the suction/irrigation tube protrudes distally from the inner tube.

In some embodiments, the endocranial endoscope can further include a hollow tube (804a) that surrounds a distal portion of the suction/irrigation tube and has a distal end that protrudes distally from the inner tube and is beveled in a shape of a hypodermic needle. In some embodiments, the suction/irrigation tube has a distal end (8a) that is beveled in a shape of a hypodermic needle, and some embodiments include both the beveled distal end of the hollow tube and the beveled distal end of the suction irrigation tube, with the sharp ends thereof at diametrically opposite positions.

In some embodiments, the stopper comprises a rim configured for pressing against the patient's skull or other head surface while the inner tube extends into the patient's cranium to a distance limited at least in part by the position of the stopper relative to the inner tube. In some embodiments, the stopper comprises two or more wings extending radially from a central area thereof, configured to press against the patient's skull or other head surface while the inner tube extends into the patient's cranium to a distance limited at least in part by the position of the stopper relative to the inner tube. In some embodiments, the stopper comprises openings configured to allow flow of cerebrospinal fluid through said opening while the stopper is pressed against a patient's skull or other head surface and the inner tube is inserted in the patient's cranium.

In some embodiments, the one or more suction and irrigation controllers comprise one or more user-operated buttons configured to move between positions that control flow to or from the distal tip of the suction/irrigation tube. In some embodiments, the one or more suction and irrigation controllers comprise a single switch moving in one direction to connect the suction/irrigation tube to a source of suction and in another direction to connect the suction/irrigation tube to a source of irrigation material.

In some embodiments, the tilt/bend controller comprises a thumb-operated joystick. In some embodiments, the tilt/bend controller is configured to cause a bend/tilt of a distal portion of the inner tube relative to a longitudinal axis of the outer tube in at least two directions, and in some embodiments in more than two directions.

In some embodiments, the imaging module comprises a control circuit housed in the handle, and in some embodiments the endoscope includes a display operatively associated with the imaging module to display intracranial images taken therewith.

In some embodiments, the outer and middle tubes are configured for telescoping the middle tube distally out of the outer tube over a first selected range of distances, and the inner tube is configured to extend distally from the middle tube by a second selected distance, thereby causing the distal end of the inner tube and to be spaced from the distal end of the outer tube by up to a combination of the first and second selected distances.

In some embodiments of the endoscope, at least the portion thereof that extends distally from the handle is a disposable, single-use instrument supplied in sterile packaging.

In some embodiments, the endocranial endoscope comprises: an outer tube having proximal and distal portions; a middle rigid tube telescoping within the outer tube between extended and retracted positions, and a sleeve (12) extending distally from the middle tube; a stopper at a distal portion of the sleeve and a biasing element biasing the stopper in the distal direction; an inner tube within the sleeve, said inner tube being shaped, dimensioned, and configured for insertion into a patient's cranium; a suction/irrigation tube within the inner tube, configured to move between extended and retracted positions relative to the inner tube; an imaging module and an illumination module at a distal end of the inner tube, wherein the illumination module is configured to illuminate a field of view inside the patient's cranium and the imaging module is configured to take and supply images of the field of view for display to a user while the inner tube is inserted in a patient's cranium; a handle configured to be grasped by a user's hand and having a distal portion coupled to a proximal portion of the outer tube, and a proximal portion, said handle comprising: a suction port coupler and an irrigation port coupler at a proximal portion of the handle, a user-operated suction and irrigation control configured to control flow between the suction/irrigation tube and the suction and irrigation ports, respectively, and a user-operated extension-retraction control operatively associated with the suction/irrigation tube to control a degree by which a distal end of the suction/irrigation tube protrudes distally from the inner tube.

In some embodiments, the inner tube comprises a bend/tilt portion adjacent a distal end thereof and the handle comprises a bend/tilt controller operatively connected to said portion of the inner tube to control an angle of the distal end of the inner tube relative to a direction parallel to an axis of the outer tube. In some embodiments, the bend/tilt controller is configured to vary said angle in a single plane and in some embodiments in two or more planes.

In some embodiments, the stopper comprises radial extensions and spaces allowing flow through the stopper.

In some embodiments, the suction/irrigation tube has a distal end beveled to form a sharp end.

The disclosed endocranial endoscopes can be used in a method comprising: providing an outer tube, a middle rigid tube telescoping within the outer tube between extended and retracted positions, a stopper spaced distally from the middle tube and biased in the distal direction, an inner tube within the middle tube and the stopper, said inner tube being shaped, dimensioned, and configured for insertion into a patient's cranium, and a suction/irrigation tube within the inner tube, configured to move between extended and retracted positions relative to the inner tube; inserting a distal portion of the inner tube into the cranium of a patient, through a prepared opening therein, until the stopper presses against the patient's cranium or a cranium-associated surface; selectively inserting the inner tube further against the biasing of the stopper; selectively extending the distal end of the suction/irrigation tube distally from the inner tube; selectively applying suction and irrigation to selected varying degrees to the suction/irrigation tube by user controllers of a handle mechanically secured to the outer tube; selectively illuminating a field of view in the patient's cranium with a light source at a distal end of the inner tube and imaging the field of view with a miniature video camera at a distal end of the inner tube; and displaying images taken with the video camera.

BRIEF DESCRIPTION OF THE DRAWINGS

FIGS. 1a and 1b are side elevation and plan view, respectively, of an example of an endoscope.

FIGS. 1c-1e illustrate an example of valves controlling suction/irrigation operations of examples of the endoscope.

FIGS. 4a, 4b, and 4c illustrate an example of a single button controlling both extension/retraction of the suction/irrigation tube and supply of suction/irrigation to the tube depending on the travel of a finger-operated button.

FIGS. 6a-6c are perspective views of an example of an endoscope with a stopper with openings for the passage of material such as cerebrospinal fluid.

FIGS. 9a and 9b illustrate an example of an endoscope handle.

DETAILED DESCRIPTION OF EXAMPLES OF PREFERRED EMBODIMENTS

Figure 2A:
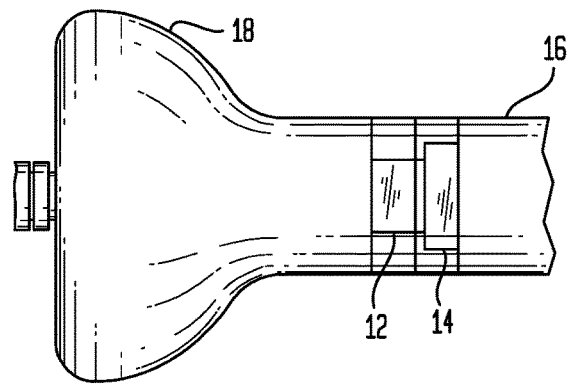
FIGS. 2a-2d are partial views of distal portions of an endoscope that can be used in the endoscope of FIGS. 1a and 1b or in other examples of endoscopes.
Figure 2B:
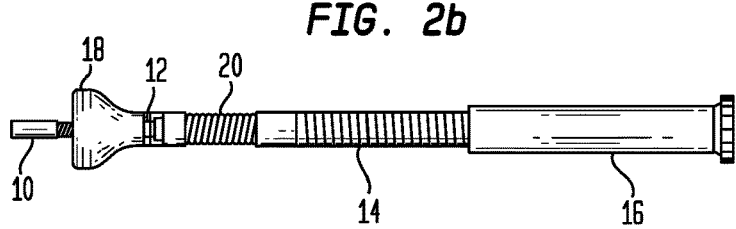
Figure 2C:
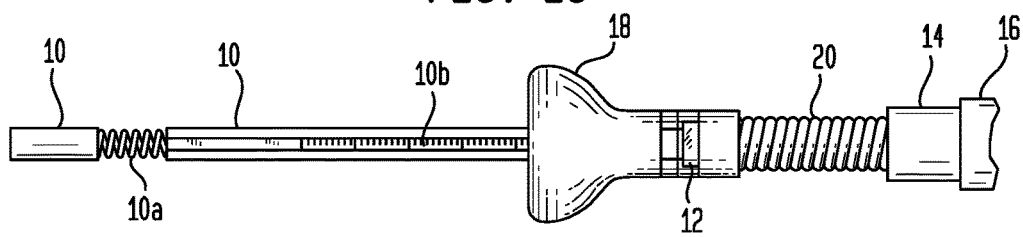

FIGS. 1a and 1b illustrate one example of an endoscope and FIGS. 2a-2d illustrate distal portions that can be a part of the endoscope of FIGS. 1a and 1b or of alternative endoscope designs. An inner tube 10 protrudes in a distal direction from a sleeve (12) that in turn protrudes distally from an externally threaded middle tube 14. Tube 14 in turn protrudes distally from and threads into an internally threaded, rigid outer tube 16. Inner tube 10 has near its distal end a bending portion 10a that can bend such that the distal end of inner tube 10 points in a direction (and the associated opposite direction) that is within a range of angles from the common axis or parallel axes of sleeve 12 and tubes 14 and 16. A depth indicator ruler 10*b* (FIG. 2*c*) extends proximally from a specified distance from the distal tip of tube 10. A stopper 18 slides over sleeve 12 between a distal position (FIG. 2*b*) to which it is biased by a spring or other biasing element 20 and a position closer to or against middle tube 14 (FIG. 2*c*). In use of the endoscope, stopper 18 typically presses against the patient's skull, or scalp, or nostril, or outer ear to provide stability and precision for surgical procedures. Inner tube 10 encloses a suction/irrigation tube 8 that slides within tube 10 between an extended position (FIG. 2*d*) in which it protrudes distally from inner tube 10 and a retracted position (FIG. 2*c*) in which it does not protrude from tube 10 or protrudes minimally from tube 10. The motion range can be 3-30 mm but other ranges can be designed as needed or desired. Tube 10 is typically made of metal, plastic, or combinations of metal and plastics and is rigid except for its portion 10*a* that bends or tilts, and tube 8 typically is made of a plastic material that is less rigid.

The distance by which middle tube 14 extends distally from outer tube 16 is adjusted by rotating the two threaded tubes with respect to each other (typically by rotating tube 14 while holding tube 16). The engaging threads operate to change the distance over a range such as 70 mm, from a maximum (FIG. 1*a*) to a minimum (FIG. 1*b*) but other ranges can be designed to suit particular endoscopic needs. In this example, the distance between stopper 18 and the distal end of outer tube 16 ranges from a total of 100 mm (70 mm due to threading and thus telescoping tube 14 into tube 16 plus 30 mm compression of bias element 20) to zero or near zero, but other ranges can be designed as needed or desired. In effect, tube 14 telescopes out of tube 16, and tube 10 telescopes out of sleeve 12.

Figure 2D:
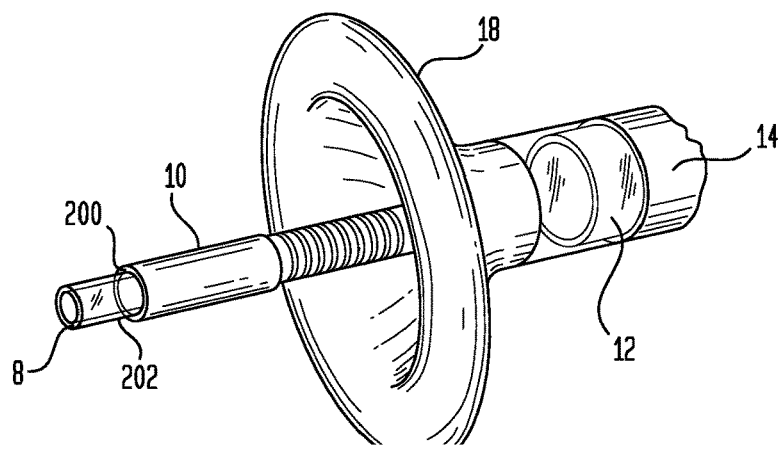

The distal tip of tube 10 encloses an imaging module comprising a miniature video camera 200 and an illumination source comprising an LED light or an optic fiber end 202 that are that are indicated by general location in FIG. 2*d* and an example of which is illustrated in more detail in FIGS. 7*a*, 7*b*, and 8 described further below. The imaging and/or illumination modules may be connected to finger controller(s) described below and to an outside display 112 via a cable 110 or wirelessly. The modules may be powered via cable 110 from a power source that may be included in display 112 and/or from internal power source(s) such as a battery or batteries.

FIGS. 1*a* and 1*b* further illustrate a handle 100 with a distal end coupled to the proximal end of outer tube 16 and provided with a tilt/bend controller 201, which in this example is a roller, coupled to bending/tilting portion 10*a* of tube 10 to cause the distal tip of tube 10 and the distal portion of tube 8 that may protrude from tube 10 to tilt away from the axis of tube 10. Handle 100 has, at its proximal end, couplers or ports 100*a* and 100*b* to connect to respective sources 100*a*1 and 100*b*1 of suction and an irrigation material through connecting tubes illustrated as broken lines. The irrigation material can be saline or other fluid and may include treatment matter such as medication that can be in fluid form or in solid form such as powder, gel, crystal, and other matrices that can be carried in fluid flow. Couplers or ports 100*a* and 100*b* connect to suction/irrigation tube 8 through respective internal passages or conduits and valves (not shown in FIGS. 1*a*-1*e*) under the control of a suction controller such as button 100*c* and irrigation controller such as button 100*d*. (In some other examples, a single controller for suction/irrigation can be used.) As button 100*c* is progressively pushed down against a bias (with an example illustrated in FIG. 1*e*) more suction is applied to tube 8. When button 100*c* is released, the fluid flow connection of tube 8 to suction coupler or port 100*a* is closed (with an example illustrated in FIG. 1*d*). As irrigation button 100*d* is pushed against bias (with an example illustrated also in FIG. 1*e*), more irrigation material is supplied to tube 8, and when button 100*d* is released the fluid flow connection between tube 8 and irrigation coupler 100*b* is closed (with an example illustrated also in FIG. 1*d*). One or both of couplers or ports 100*a* and 100*b* can include electrical wires and/or one or more optical fibers connecting outside electronics and/or light sources to an imaging module such as a camera 200 and an illumination module such as a light source 202 at the tip of tube 10, or handle 100 can include respective separate electrical and/or fiber optic connectors (not shown) for the purpose. Handle 100 typically encloses electrical circuitry involved in the operation of video camera 200 and/or light source 202, such as controller chips and other circuitry to operate the video camera and the light source, and the handle may have hand or finger operated controllers for turning on and off one or both of the video camera and the light source or for selecting between video clips and stills and/or for otherwise controlling the imaging and/or illumination modules. In addition, in this example handle 100 includes controllers in the form of side sliders 204 and 208 that slide in the distal-proximal direction to extend tube 8 distally from the tip of tube 10 (to a position seen in FIG. 2*d*) or retract it into tube 10. The range of tube 8 extension can be 5 mm but other ranges can be designed. Still in addition, handle 100 can include a controller in the form of a joystick or other interface associated with tube 8 to control tilting of the extended portion of tube 8 (FIG. 2*d*) relative to the axis of tube 10, which tilting control and tilted position of the tip of tube 8 are not shown in FIGS. 1*a* and 1*b* but are illustrated in and discussed in connection with other figures further below.

FIGS. 1*c*, 1*d* and 1*e* illustrate an example of a fluid flow connection between couplers/ports 100*a* and 100*b* and the distal portion of tube 8 and of valves to control the fluid flow. As seen in a schematic view in FIG. 1*c*, suction port 100*a* connects to a conduit 124 controlled by a valve 126 operated with button 100*c*, and irrigation coupler/port 100*b* connects to conduit 114 controlled by a valve 116 operated by irrigation button 100*d*. Conduits 124 and 114 merge into the distal portion of tube 8 (or into a conduit that is in fluid flow communication with the distal portion of tube 8) to thereby enable fluid flow between the distal portion of tube 8 and coupler/ports 100*a* and 100*b*. FIGS. 1*d* and 1*e* illustrate an example of a valve that can be used for valve 112 and/or valve 114. In this example, the valve comprises a movable cylinder 118 that slides inside a host cylinder 120 against the bias of a spring 122. Each cylinder has a transverse opening though which conduit 124 (or 114) passes. Conduits 124 and 114 are made of a material sufficiently pliable to compress and thus reduce or stop fluid flow when compressed between the movable and host cylinders, and sufficiently resilient to open up and thus allow flow when not pinched between the two cylinders. Spring 122 pushes the two cylinders to keep the valve closed, preventing fluid flow through conduit 124 (114). When button 100*a* (100*b*) is pushed down via button 100*c* (100*d*) against the force of spring 122, for example to the position seen in FIG. 1*e*, the two cylinders separate sufficiently to allow fluid flow through an oval-shaped cross-section of conduit 124 (114). Pushing down further allows more flow, until the conduit assumes a circular cross-section, and releasing pressure on button 100*c* (100*d*) gradually reduces flow until pressure is sufficiently released to allow spring 122 to push cylinder 118 sufficiently up from host cylinder 120, as seen in FIG. 1d. Other examples of valves can be used to control fluid flow between the distal tip of tube 8 and the suction/irrigation ports, some of which are discussed further below.

Bend/tilt control over the distal tip of tube 10 and thus tube 8 can be accomplished, for example, with wires connected to diametrically opposite sides of the tip of tube 10, distally of bend/tilt portion 10a. The can be controlled by twisting knob 201 to thereby shorten one of two diametrically opposed wires, for example by cam action. Another example is discussed in more detail in connection with FIGS. 3a and 3b below.

Some or all of the portions distal from the handle of the endoscopes described in this patent specification can be single-use, disposable components that are configured to be supplied in sterile packaging and assembled with one of the described handles, preferably by hand and without tools, through use of mating mechanical/electrical couplers to establish the necessary mechanical/electrical connections for the operations this patent specification describes. Alternatively, some or all of the endoscopes described in this patent specification can be disposable, single-use devices that are used only once for a procedure on a patient.

Figure 3A:
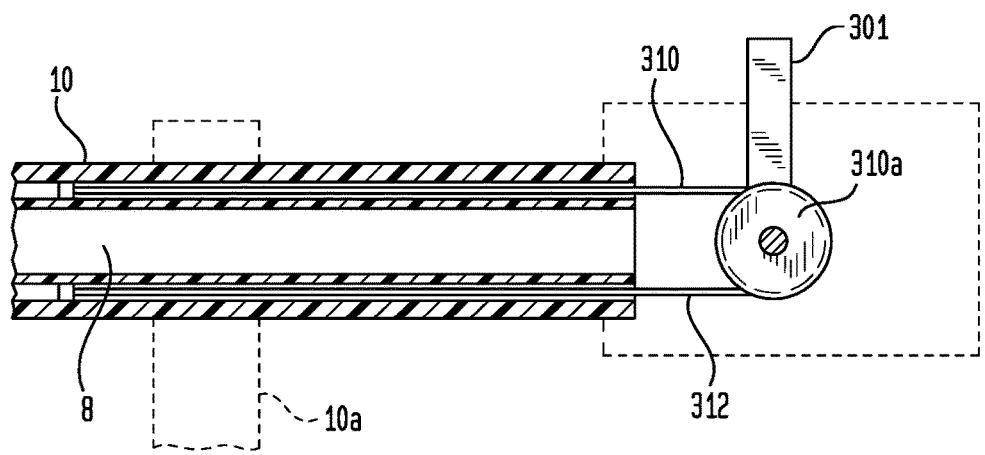
FIGS. 3a and 3b illustrate an example of a mechanism for bending/tilting a distal tip of endoscope examples.
Figure 3B:
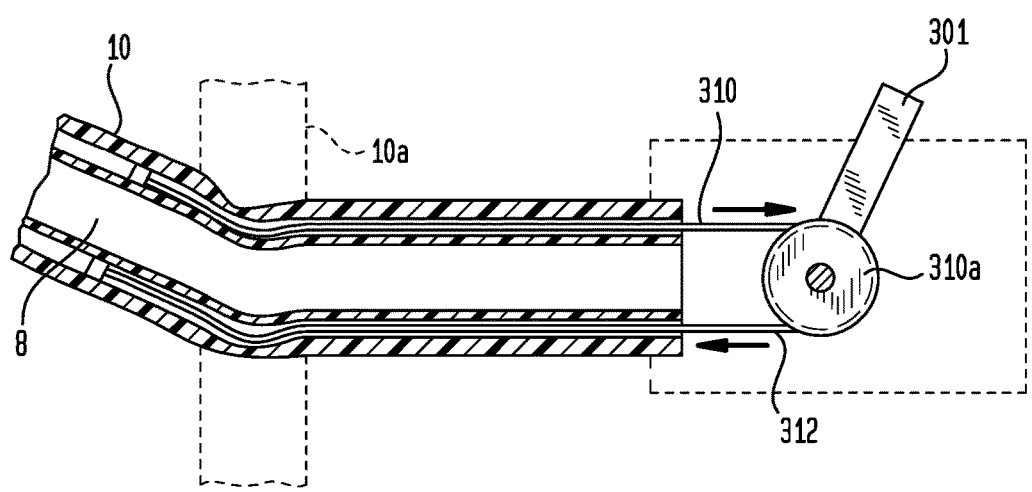

FIGS. 3a and 3b illustrate and example of controlling bend/tilt of the distal tip of tube 10 and thus of tube 8. Button 301 can be a sliding button or a joystick as schematically shown in FIGS. 3a and 3b. It can extend up (not shown in the figure) through the top of handle 100 from a wheel 310a mounted for rotation inside handle 100 and drives a wire portion 310 and wire portion 312 that are secured to the top and bottom, respectively, of the tip portion of tube 10, distally of the bend/tilt portion 10a, and are secured to wheel 310a operated by switch or joystick 301. Pulling switch or joystick 301 back relative to handle 100 bends/tilts the tip of tube 10 and thus of tube 8 up, as seen in FIG. 3b, and pushing switch/joystick 301 forward bends/tilts the tips of tubes 10 and 8 down. If an additional pair of wires (not shown) is used such that their distal ends are secured to the tip of tube 10, so that there is a wire secured at each quarter of the tip of tube 10, and a ball rather than a wheel 310a is secured to button/joystick 301, with the wires connected at four sides of the ball, then moving button/joystick 301 sideways bends/tilts the tips of tubes 10 and 8 left or right as well. Intermediate directions of moving button/joystick 301 relative to handle 100 can accomplish bending/tilting the tips of tubes 10 and 8 in any desired direction.

Figure 4D:
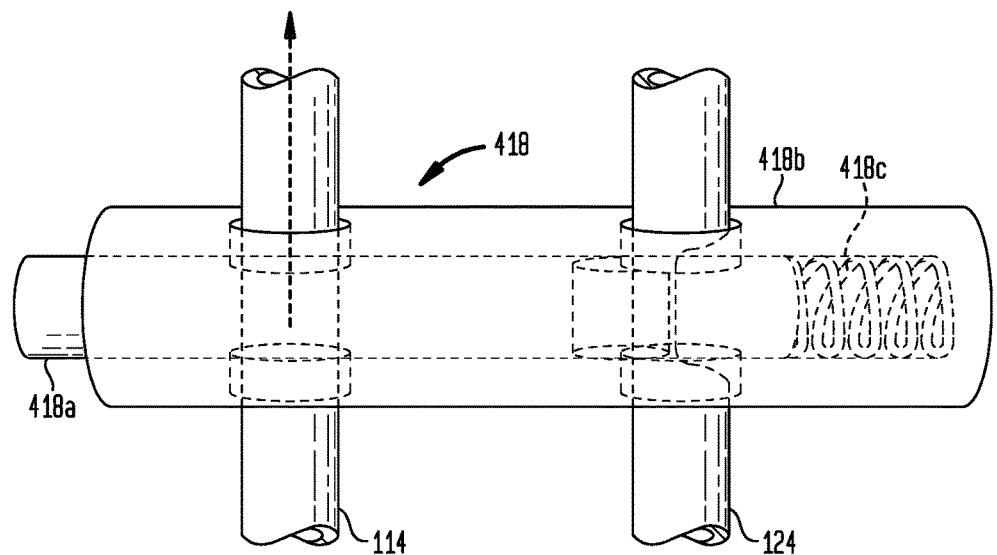
FIGS. 4d and 4e illustrate an example of a valve arrangement useful in the mechanism of FIGS. 4a-4c.

FIGS. 4a, 4b, and 4c illustrate an example of a mechanism that uses a controller to control both extending tube 8 distally out of tube 10 and suction/irrigation, which can be used inside one or more of the handles described in this specification except that a button 410 is accessible from outside the handle, either directly or through an intermediate button or lever. In this example, a button 410 drives a lever 412 that is pivoted at 414 inside a handle and has its other end secured to tube 8 (which is made of a flexible material). FIG. 4a shows a neutral position of the controller, in which tube 8 is in a retracted position relative to tube 10 and a spring 416 biases lever 412 to that position (and curves up a portion of tube 8). As button 410 is pushed into the handle, against the bias of spring 416, lever 412 starts pushing tube 8 in the distal direction. For some distance of the button's initial travel relative to the handle, such as the first 1.8 mm of travel, button 410 remains out of contact with a valve 418, so the valve remains in its neutral position up to the point tube 8 extends out of tube 10 by a selected distance such a 1 mm. In this position, illustrated in FIG. 4b, tube 8 is curved somewhat less than in FIG. 4a. As button 410 is pushed further into the handle, still against the bias of spring 416, it contacts valve 418 and starts acting on it as described below in connection with FIGS. 4d and 4e, to thereby reduce and eventually stop irrigation and start and increase suction. Meanwhile, the lever pushes the tube 8 to extend more, up to 3 mm or 5.5 mm, out of tube 10, and tube 8 straightens out as illustrated in FIG. 4c. One benefit of the initial extension of tube 8 out of tube 10, by the initial travel down of button 410, is that the surgeon can use the extended portion of tube 8 to poke and disrupt a blood clot without applying suction, and then press button 410 further down to apply suction and extract matter that may include already disrupted and broken up material.

Figure 4E:
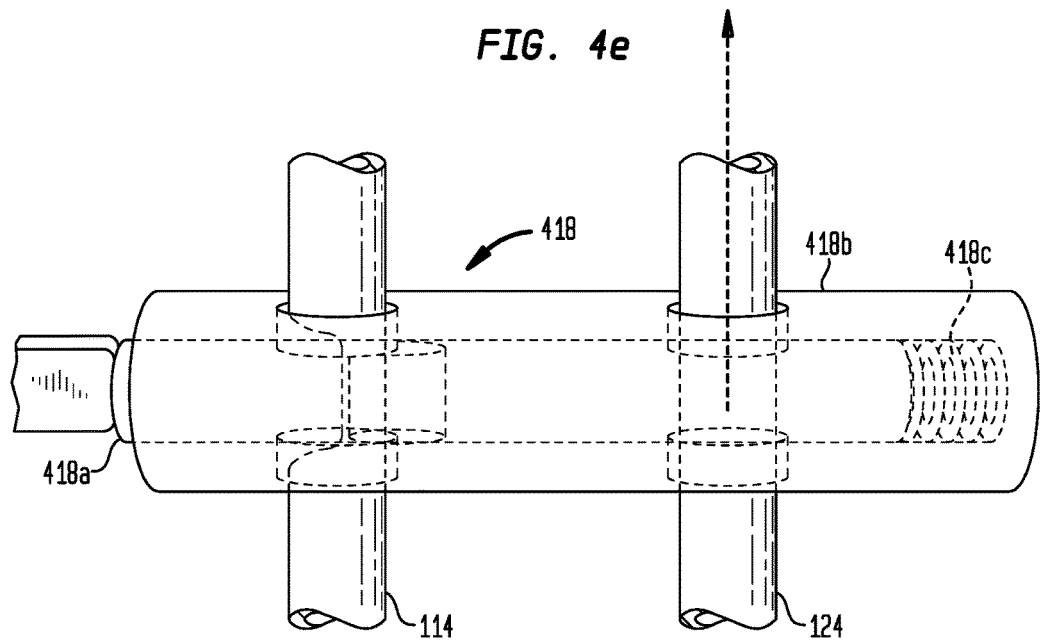

FIGS. 4d and 4e illustrate an example of a valve 418 (also seen in FIGS. 4a-4c) that controls both suction and irrigation. Valve 418 comprises a movable cylinder 418a sliding inside a host cylinder 418b. Suction tube 124 and irrigation tube 114 pass through respective openings in both cylinders, but the openings are set up such that when the openings for the suction tube are sufficiently misaligned to pinch suction tube 124 and block flow through it, the openings for irrigation tube are aligned to not pinch irrigation tube 114 and thus allow flow of irrigation material to the distal end of tube 8. Conversely, when irrigation tube 114 is pinched to stop flow through it, suction tube 124 is not pinched and allows suction from the distal tip of tube 8. A spring 418c biases the two cylinders such that in a normal state of valve 418 irrigation tube 114 is open (not pinched) but suction tube 124 is pinched and blocked. As button 410 makes contact with valve 418 and starts moving to the right in FIGS. 4d and 4e, irrigation tube 114 is gradually pinched more while suction tube 124 is gradually opened more, so the distal tip of tube 8 gradually changes from full irrigation and no suction to full suction and no irrigation. This arrangement facilitates irrigating an anatomical site while tube 8 is retracted, then extending tube 8 distally while still irrigating, to help dislodge tissue that should be removed, and then changing over to suction to remove tissue. As an alternative, the openings in cylinders 418a and 418b can be aligned such that there is neither suction nor irrigation in a neutral state of valve 418 but irrigation or suction starts as button 410 contacts valve 418 and irrigation or suction increases as the button is pushed further and then there is a changeover from one of irrigation and suction to the other.

Figure 5:
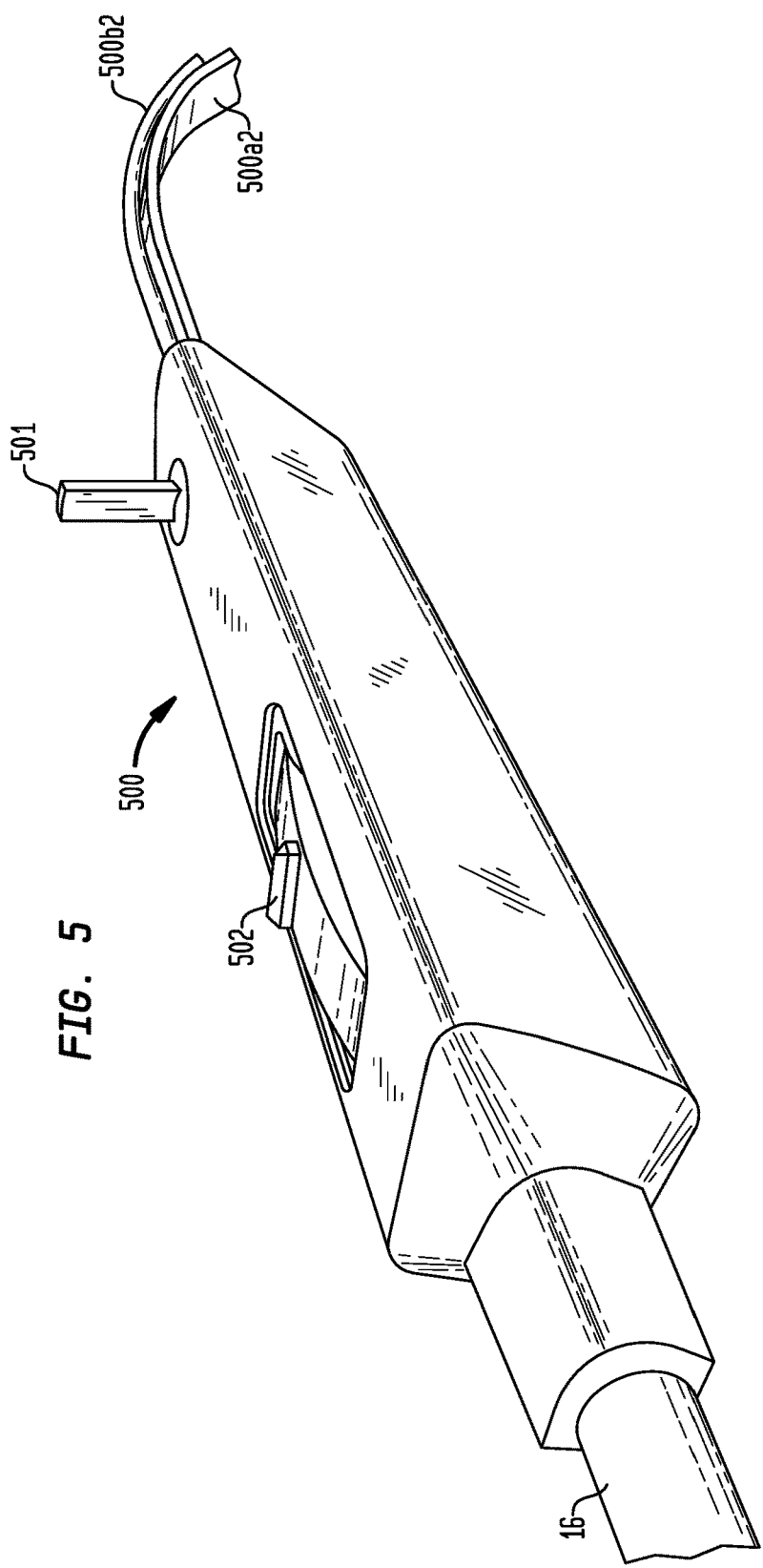
FIG. 5 is a perspective view of an example of a handle of an endoscope and of conduits for connection to sources of suction and irrigation.

FIG. 5 illustrates an example of a handle 500 that can be used with any of the components described herein that extend distally from handles such as 100. The portion of handle 500 that the user's hand grasps can be made of relatively soft material, at least for a layer on or near its outside surface, such as rubber or rubber-like material, to increase the user's comfort and make slippage between the handle and the user's hand less likely. Handle 500 as illustrated has a generally rectangular cross-section with rounded edges but a generally triangular cross-section with rounded edges is an alternative that is contemplated. Handle 500 comprises a suction/irrigation controller 502 that can be in the form of a slider operating valves that gradually open/close the fluid flow path between tube 8 and tube 500a2 leading to a source of suction and tube 500b2 leading to a source of irrigation material. For example, when the user's thumb gradually pushes slider 502 forward, in the distal direction, suction is applied to tube 8 and the degree of suction rises with the distance to which slider 502 is pushed in the distal direction. When the user gradually pushes slider 502 backward, in the proximal direction, irrigation is supplied to tube 8 and the irrigation flow gradually increases as slider 502 is pushed more in the proximal direction. In this example, slider 502 is biased to a neutral central position at which neither suction nor irrigation is applied to tube 8, and returns to that position when the user is not pushing slider 502 in either direction, and can use the alternative arrangement of valve 418 described above. Handle 500 further comprises an articulation controller 501, coupled with the bend/tilt portion 10*a* of tube 10 to articulate the distal end of tube 10 relative to the axes of tubes 14 and 16, for example in the left-right direction, the up-down direction, or any other direction.

FIGS. 6*a*, 6*b*, and 6*c* are perspective views illustrating a stopper 618 that is an important alternative to stopper 18 of FIGS. 1*a* through 2*d*. Stopper 618 has openings through which excess cerebrospinal fluid can drain, and the openings also can avoid increasing intracranial pressure. Stopper 618 can be used in place of stopper 18 in any of the examples of endoscopes discussed herein. Stopper 618 comprises a round or circular rim 618*a* and three spokes 618*b* extending distally as they spread out from a sleeve 618*c* secured to sleeve 12. In use, stopper 618 is pressed against the patient's skull or other head surface, as in the case of stopper 18, while the distal tip of the endoscope treats matter inside the skull. Stopper 618 can further provide a navigation function, for example by making one or more of its spokes longer or shorter than another spoke or other spokes, which can help control and assess the direction of insertion of the endoscope relative to the surface against which stopper 618 is pressed, or by including other navigation aids that help identify the position and/or direction of the portion of tube 10 that is inside the cranium in the course of a surgical or exploratory procedure. Rim 618*a* and spokes 618*b* can be made of the same material, which may be sufficiently stiff to retain shape during use of the endoscope, or the spokes and rim 618*a* can be made of materials with different stiffness or softness as desired or suited to different surgical or exploratory procedures. FIGS. 6*b* and 6*c* illustrate stopper 618 as a part of an endoscope having a handle 600 that can be the same as handle 500 in FIG. 5, and suction/irrigation conduits 600*a*1 and 600*b*2 serving the same functions as conduits 500*a*2 and 500*b*2 in FIG. 5. FIGS. 6*b* and 6*c* additionally illustrate a conduit 600*f* that can contain wires supplying power and/or carrying control and image data to and/or from the imaging module that includes a video camera at the distal tip of the endoscope (not seen in FIGS. 6*a*-6*c*) and/or carrying power, light, or control signals to the illumination module that includes a light source at the tip of the endoscope (also not seen in FIGS. 6*a*-6*c*).

Figure 6D:
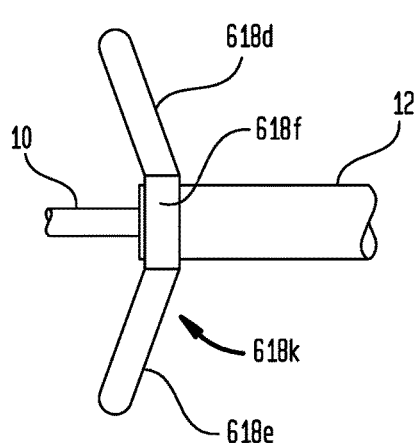
FIGS. 6d and 6e illustrate an alternative stopper.
Figure 6E:
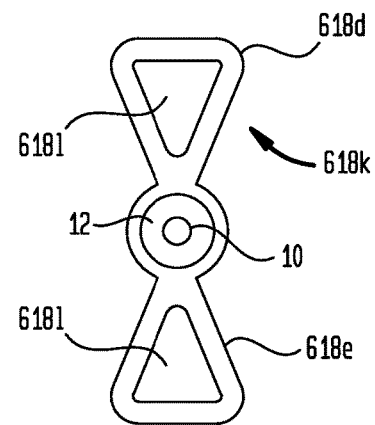

FIGS. 6*d* and 6*e* illustrate an alternative stopper 618*k* that can be used in any of the endoscopes described herein in place of the stoppers described above. Stopper 618*k* comprises a pair of wings 618*d* and 618*e* extending radially in opposite directions from a central portion 618*f* that surrounds tube 12. Each wing has a central opening 6181 configured to allow fluid flow therethrough when the stopper is pressed against the patient's skull or other head surface. More than two wings can be used in alternative stoppers, preferably distributed uniformly around the circumference of the stopper. The illustrated wings are triangular, with central openings and apices at the central area of the stopper, but other shapes are possible, such as strips, rectangles and ovals, to name a few. Preferably, the wings are made of a material that is relatively soft so it would not damage patient tissue and yet is sufficiently stiff and resilient so the wings are spring-like when pressed against a surface.

Figure 7B:
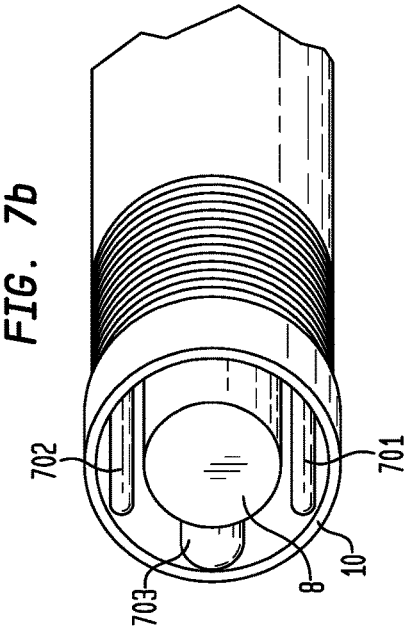
FIGS. 7a-7c are perspective views of one example of a distal tip of an endoscope.
Figure 7A:
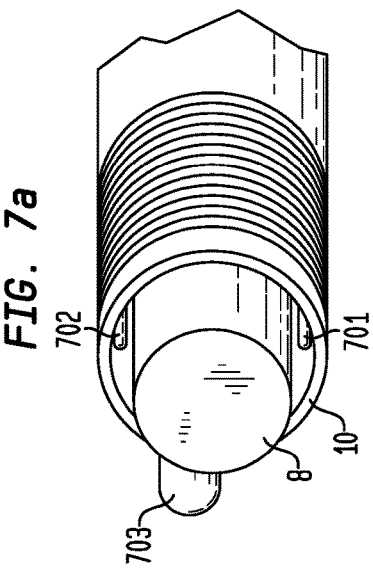

FIGS. 7*a*-7*b* are perspective views of one example of a distal tip of an endoscope. FIGS. 7*a* and 7*b* illustrate a distal end that can be used in any of the endoscopes described above. The distal end includes forward-facing (in the distal direction) portions of an imaging module and an illumination module, namely, light sources 701 and 702, which can be LED lights or the ends of optical fibers, and a forward facing video camera 703 such as a CMOS camera. Inner tube 10 surrounds suction/irrigation tube 8 as well as the light sources and the video camera. In one example of the endoscope, the outside diameter of camera 703 can be 1.4 mm, the outside diameter of suction/irrigation tube 8 can be 2.8 mm, the diameter of each of the optical fibers can be less than 0.4 mm (or LEDs of comparable diameters can be used instead), and the outside diameter of inner tube 10 can be 5.3 mm.

Figure 7C:
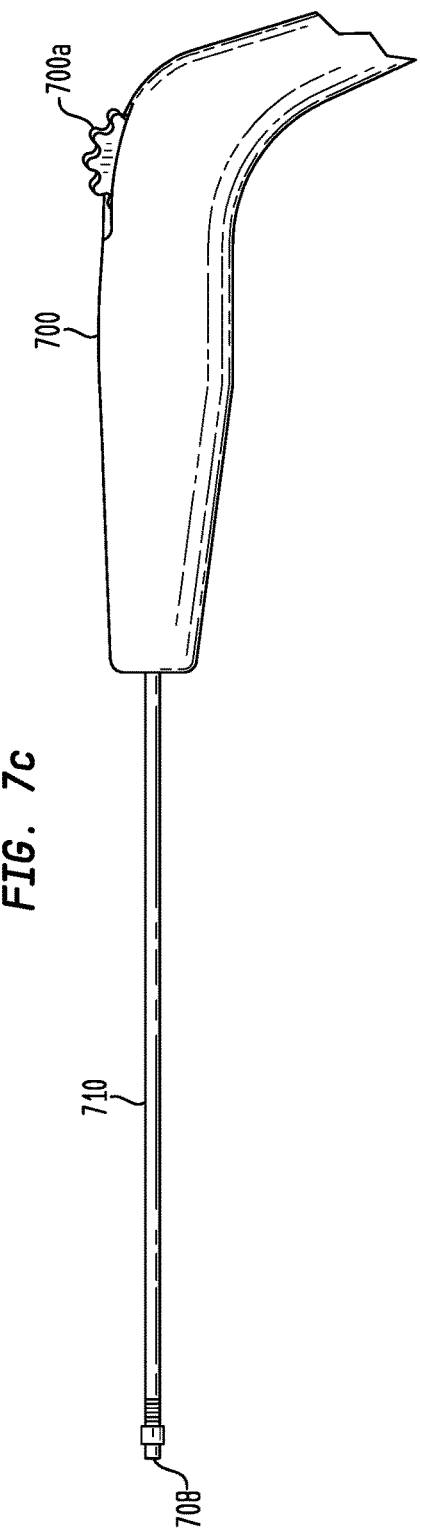

FIG. 7*c* illustrates an endoscope in which a tube 710 for insertion into a patient's cranium extends 180 mm distally from a handle 700 and suction/irrigation tube 708 can extend up to 5 mm distally from tube 710, as selected by thumbwheel controller 700*a*.

Figure 8:
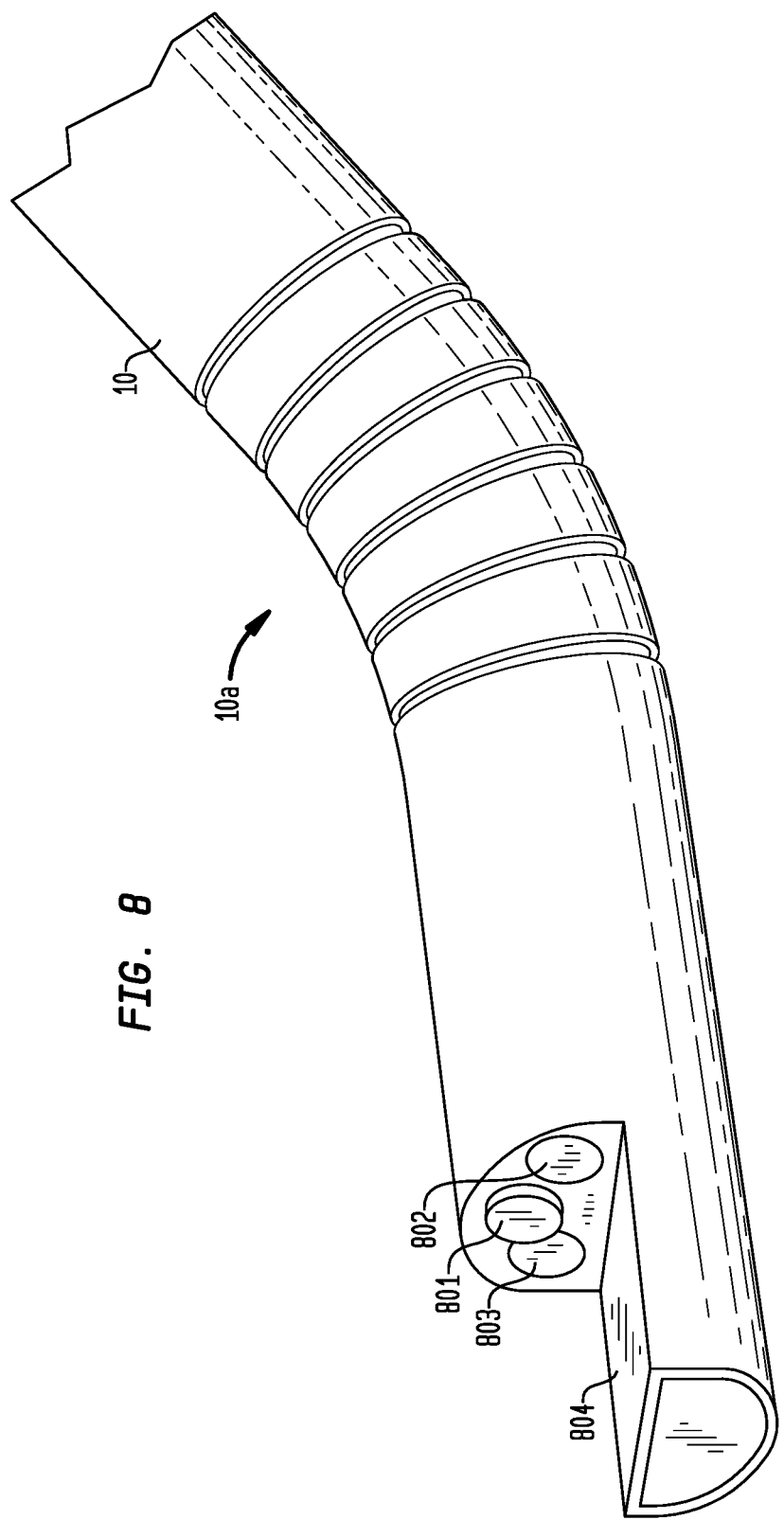
FIG. 8 is a perspective view of an alternative distal end of endoscopes.

FIG. 8 illustrates in a perspective view an example of a distal tip that can be used with any of the endoscopes described herein. This example has an illumination module with forward looking LED lights 802 and 803 and an imaging module with forward looking video camera 801, and a projection 804 that preferably is transparent to light from the illumination module and extends in the distal direction from inner tube 10. In addition, the illustrated tip can include a suction/irrigation tube (not expressly shown in FIG. 8) with a forward looking opening and/or a side opening. For example, tube 8 can extend in a channel in inner tube 10 and protrude distally from tube 10 as desired.

Figure 8A:
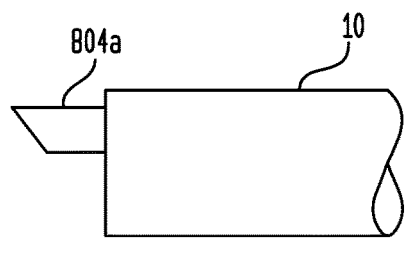
FIGS. 8a-8c illustrate an alternative distal end for an endoscope.
Figure 8B:
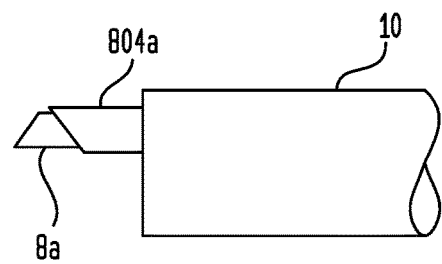
Figure 8C:
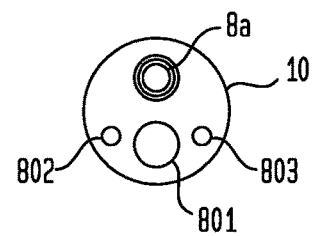

FIGS. 8*a*-8*c* illustrate an alternative distal portion that can be used in any of the endoscopes described herein in place of the distal portions described above. The side elevations of FIGS. 8*a* and 8*b* show the distal end of inner tube 10, from which a hollow tube 804*a* protrudes in the distal direction. Tube 804*a* preferably is beveled, to a shape of a hypodermic needle, and terminates in a sharp point. The side elevation of FIG. 8*b* shows a distal portion 8*a* of suction/irrigation tube 8 protruding distally from hollow tube 804*a*. Preferably, the distal end of tube portion 8*a* also is beveled like a hypodermic needle, with a sharp point that preferably but not necessarily is diametrically opposite the sharp point of tube 804*a*. The front view of FIG. 8*c* illustrates an arrangement of elements in inner tube 10: hollow tube 804*a* and suction/irrigation tube portion 8*a* therein, imaging module 801, and light sources 802, 803. In use, after inner tube is inserted in the patient's cranium the beveled tip of hollow tube 804*a* can help penetrate and/or break up tissue such as coagulated blood, and the beveled end of suction/irrigation portion 8*a* can then be extended distally to further held bread down coagulated blood or other material and irrigate the side or suck out fluids or tissue.

Figure 9B:
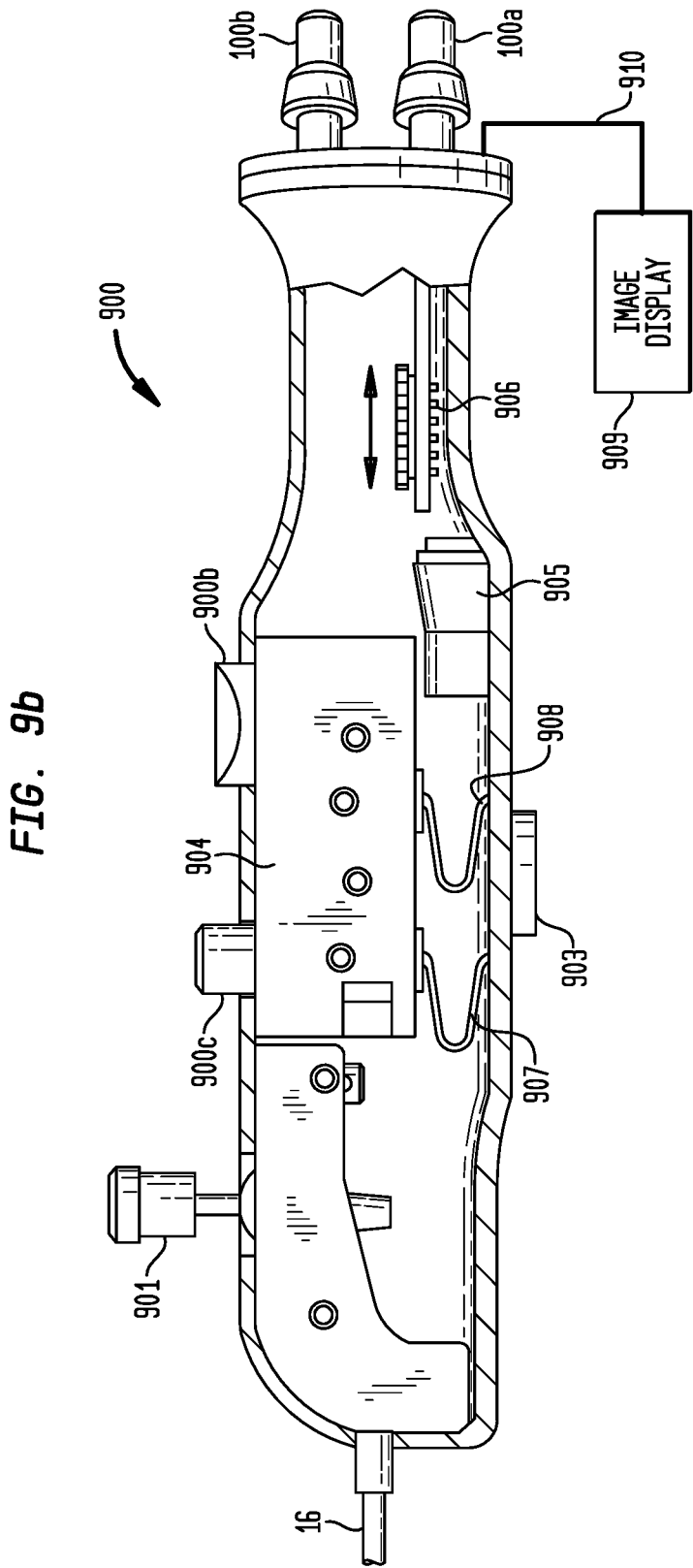

FIG. 9*a* is a side elevation and FIG. 9*b* is a side view of an example of a handle 900 that can be used in any of the endoscopes in place of the handles described above. Handle 900 comprises a bend/tilt control 901, and an irrigation controller in the form of a button 900*c* and a suction controller in the form of a slider 900*b* that control fluid flow between suction/irrigation tube 8 (not seen in FIGS. 9*a* and 9*b*) and irrigation coupler 100*b* and suction coupled 100*a*, respectively. In addition, handle 900 comprises a brightness controller in the form of a wheel 902 that the user can rotate to increase or decrease the brightness of LEDs such as 701, 702 in FIGS. 7*a* and 7*b* or 802 and 803 in FIG. 8. Still in addition, handle 900 can include one or more finger-operated controllers 903 that control a video camera such as 703 in FIGS. 7a and 7b or 801 in FIG. 8, for example to turn the camera ON and OFF, and/or to control other functions such as selecting between video clips and stills, or selecting between different modes of operation of the camera such as different resolutions, frames per second, etc.

FIG. 9b illustrates some of the internal components of handle 900, which can be the same as or similar to internal components of the other examples of handles described above. FIG. 9b illustrates valves 904 controlling fluid flow between suction/irrigation tube 8 (not seen in FIG. 9b) and suction and irrigation couplers 100a and 100b, spring 907 biasing irrigation controller 900c to its position in which it closes the fluid flow connection between tube 8 and conduit 100b, and spring 908 biasing the suction control 900b to a position in which it closes the fluid flow connection of tube 8 to suction coupler 100a. In addition, FIG. 9b illustrates an internal circuit board 905 (connected to LEDs 701, 702 or 802, 803 and to brightness control 902) to provide power and control to the LEDs, for example from an internal battery or from an external power source to which it connects though a cable such as 600f in the example of FIGS. 6b and 6c. FIG. 9b also illustrates a circuit board 906 coupled with a video camera at the distal tip of the endoscope, such as camera 703 or 801, and to controllers 903 to provide power and control signals to the camera and to carry images taken with the camera to an external display 909 over a cable 910 or through a wireless connection.

Figure 10A:
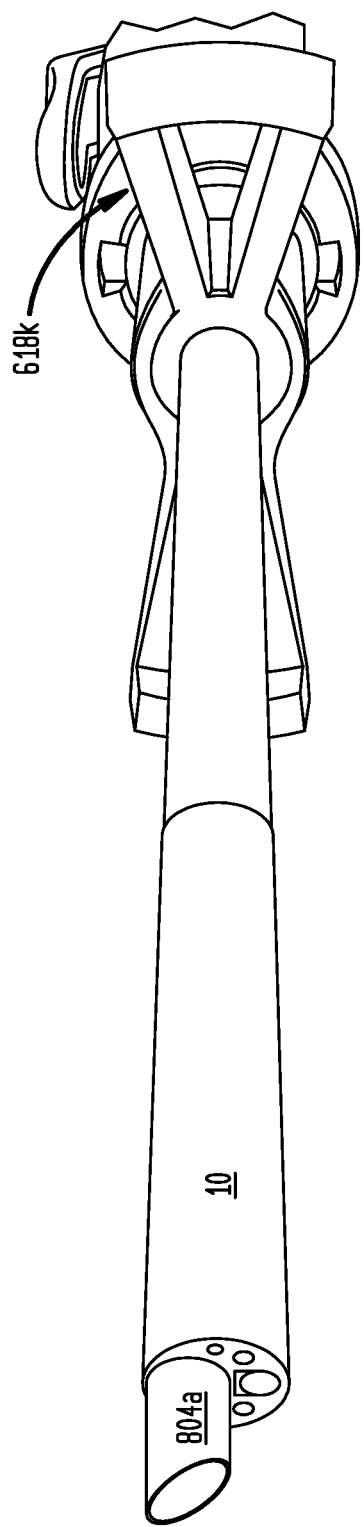
FIGS. 10a and 10b illustrate alternative embodiments of portions of an intracranial endoscope.
Figure 10B:
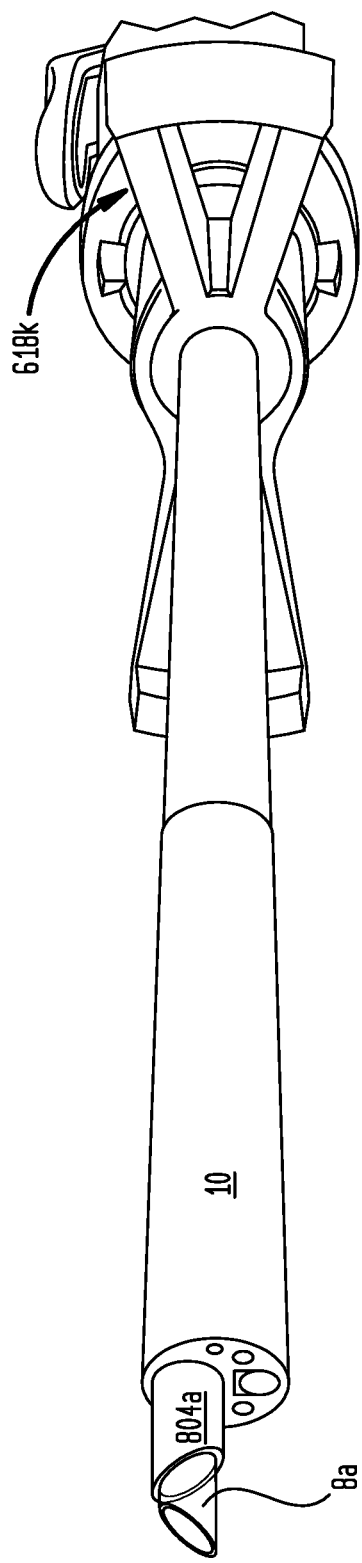

FIGS. 10a and 10b illustrate in perspective the distal portion of an endoscope that uses the stopper illustrated in FIGS. 6d and 6e and the distal portion illustrated in FIGS. 8a-8c. In FIG. 10a, the suction/irrigation tube 8 (and its distal portion 8a) are retracted and not seen. In FIG. 10b, the distal portion 8a of suction/irrigation tube 8 is shown protruding distally.

Figure 11:
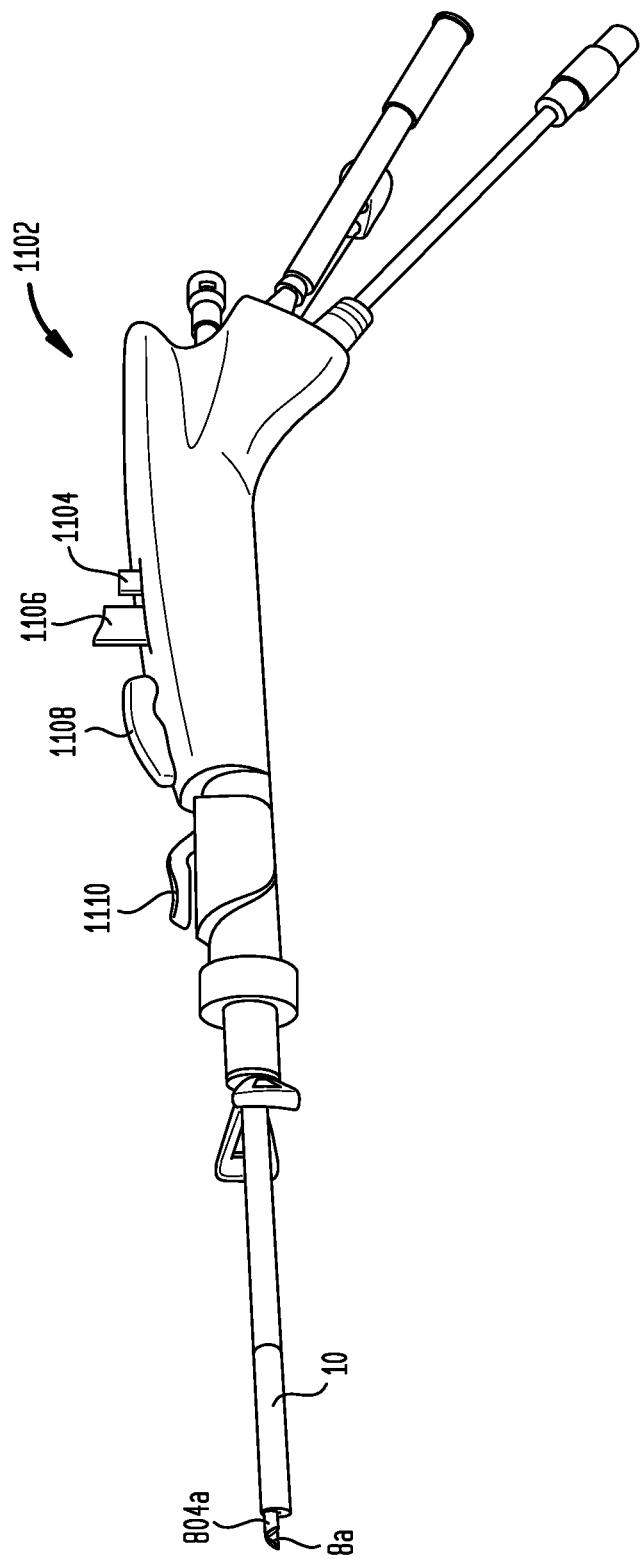
FIG. 11 is a perspective view of an alternative embodiments of an intracranial endoscope.

FIG. 11 shows in perspective an endoscope example that uses the portions illustrated in FIGS. 10a and 10b, and can use any of the features of the other endoscope examples disclosed herein. FIG. 11 further illustrates a handle 1102 that can be used for any of the endoscope examples disclosed herein in place of the other described handles. Handle includes controls that can be in the form of slide switches, buttons, joysticks (or other user-operated controls) 1104, 1106, and 1108 that can control the functions described above for other handles, such as extending and retracting the suction/irrigation tube 8, controlling suction and irrigation flow through tube 8 and its distal portion 8a, bending/tilting the distal portion of inner tube 10, etc. FIG. 11 further illustrates two conduits couples with the proximal portion of handle 1102 and connected to suction and irrigation sources, and at least one electrical cable to connect electrical power sources for the video module and light sources at the tip of the endoscope, and to connect the video module to a video display screen and/or memory or other devices to which sills or video clips from the video module should be supplied.

While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all of these details. Moreover, for clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

Various modifications may be made without departing from the spirit and scope of the new methods and systems described in this patent specification. Accordingly, the scope of this patent specification is not limited to the above-described embodiments, but instead is defined by the claims of a patent to issue thereon in light of their full scope of equivalents.

The invention claimed is:

1. An endocranial endoscope comprising:
   an internally threaded, rigid outer tube having proximal and distal portions;
   an externally threaded middle rigid tube threaded into the outer tube for relative rotation therewith to thereby telescope between extended and retracted positions;
   an inner tube that has a proximal portion partly in the middle tube and a distal portion that is shaped, dimensioned, and configured for insertion into a patient's cranium;
   a stopper mounted distally of the middle tube to move axially relative to the middle tube, and a biasing element biasing the stopper in a distal direction relative to the middle tube;
   wherein the inner tube has a bend/tilt portion adjacent a distal end thereof, and is configured to be moved to extended and retracted positions relative to the middle tube;
   a suction/irrigation tube sliding in the inner tube between an extended position in which it protrudes distally from the inner tube and a retracted position;
   an illumination module and an imaging module at a distal end of the inner tube, wherein the illumination module is configured to illuminate a field of view inside the patient's cranium and the imaging module is configured to take and supply images of the field of view for display to a user;
   a handle configured to be grasped by a user's hand and having a distal portion coupled to the proximal portion of the outer tube, and a proximal portion, said handle comprising a suction port coupler and an irrigation port coupler at the a proximal portion of the handle, and the following user-operated controllers:
   (i) one or more suction and irrigation controllers configured to control flow between the suction/irrigation tube and the suction and irrigation ports,
   (ii) a tilt/bend controller operatively associated with the tilt/bend portion of the inner tube to control direction and degree of tilt/bend thereof; and
   (iii) an extension-retraction controller operatively associated with the suction/irrigation tube to control a degree by which a distal end of the suction/irrigation tube protrudes distally from the inner tube.

2. The endocranial endoscope of claim 1, further including a hollow tube that surrounds a distal portion of said suction/irrigation tube and has a distal end that protrudes distally from the inner tube and is beveled in a shape of a hypodermic needle.

3. The endocranial endoscope of claim 1, in which said suction/irrigation tube has a distal end that is beveled in a shape of a hypodermic needle.

4. The endocranial endoscope of claim 1, further including a hollow projection from a distal end of said inner tube, having a distal end beveled in a shape of a hypodermic needle with a sharp end, and wherein said suction/irrigation tube has a distal end that is beveled in a shape of a hypodermic needle with a sharp end, and the two sharp ends are diametrically opposed.

5. The endocranial endoscope of claim 1, wherein the stopper comprises a rim configured to press against the patient's skull or other head surface while the inner tube extends into the patient's cranium to a distance limited at least in part by the position of the stopper relative to the inner tube.

6. The endocranial endoscope of claim 1, wherein the stopper comprises two or more wings extending radially from a central area thereof, configured to press against the patient's skull or other head surface while the inner tube extends into the patient's cranium to a distance limited at least in part by the position of the stopper relative to the inner tube.

7. The endocranial endoscope of claim 1, wherein the stopper comprises openings configured to allow flow of cerebrospinal fluid through said opening while the stopper is pressed against a patient's skull or other head surface and the inner tube is inserted in the patient's cranium.

8. The endocranial endoscope of claim 1, wherein the one or more suction and irrigation controllers comprise one or more user-operated buttons configured to move between positions that control flow to or from the distal tip of the suction/irrigation tube.

9. The endocranial endoscope of claim 1, wherein the one or more suction and irrigation controllers comprise a single switch moving in one direction to connect the suction/irrigation tube to a source of suction and in another direction to connect the suction/irrigation tube to a source of irrigation material.

10. The endocranial endoscope of claim 1, wherein the tilt/bend controller comprises a thumb-operated joystick.

11. The endocranial endoscope of claim 1, wherein the tilt/bend controller is configured to cause a bend/tilt of the distal portion of the inner tube relative to a longitudinal axis of the outer tube in at least two directions.

12. The endocranial endoscope of claim 1, wherein the imaging module comprises a control circuit housed in the handle.

13. The endocranial endoscope of claim 1, further including a display operatively associated with the imaging module to display intracranial images taken therewith.

14. The endocranial endoscope of claim 1, wherein the outer and middle tubes are configured for telescoping the middle tube distally out of the outer tube over a first selected range of distances, and the inner tube is configured to extend distally from the middle tube by a second selected distance, thereby causing the distal end of the inner tube and to be spaced from the distal end of the outer tube by up to a combination of the first and second selected distances.

15. The endocranial endoscope of claim 1, wherein at least the portion thereof that extends distally from the handle is a disposable, single-use instrument supplied in sterile packaging.

* * * * *